(12) United States Patent
Cohen et al.

(10) Patent No.: US 10,245,424 B2
(45) Date of Patent: Apr. 2, 2019

(54) UV STERILIZING CATHETERS AND CATHETER CONNECTORS

(71) Applicants: Maria Patricia Cohen, Mercer Island, WA (US); Gordon Alan Cohen, Mercer Island, WA (US)

(72) Inventors: Maria Patricia Cohen, Mercer Island, WA (US); Gordon Alan Cohen, Mercer Island, WA (US)

( * ) Notice: Subject to any disclaimer, the term of this patent is extended or adjusted under 35 U.S.C. 154(b) by 780 days.

(21) Appl. No.: 14/573,911

(22) Filed: Dec. 17, 2014

(65) Prior Publication Data
US 2015/0165185 A1 Jun. 18, 2015

Related U.S. Application Data

(60) Provisional application No. 61/917,818, filed on Dec. 18, 2013.

(51) Int. Cl.
*A61M 39/16* (2006.01)
*A61M 16/04* (2006.01)
(Continued)

(52) U.S. Cl.
CPC .............. *A61M 39/16* (2013.01); *A61L 2/10* (2013.01); *A61M 16/0402* (2014.02);
(Continued)

(58) Field of Classification Search
CPC .. A61M 2039/0167; A61M 2039/0285; A61M 2025/0019; A61M 2025/0097; A61M 2025/0606; A61M 2039/167
See application file for complete search history.

(56) References Cited

U.S. PATENT DOCUMENTS 5,855,203 A * 1/1999 Matter ..................... A61L 2/10
128/207.14
6,254,625 B1 7/2001 Rosenthal et al. ............. 607/88
(Continued)

FOREIGN PATENT DOCUMENTS

JP H0523394 2/1993 ........... A61B 5/0265
RU 67448 10/2007 ............ A61M 16/04
(Continued)

OTHER PUBLICATIONS

International Search Report and Written Opinion issued in PCT/US2014/070912, dated Apr. 13, 2015 (10 pgs).
(Continued)

*Primary Examiner* — Valerie L Woodward
(74) *Attorney, Agent, or Firm* — Hayes Soloway PC

(57) ABSTRACT

A catheter connector includes an inner wall that defines an interior of the catheter connector and is transmissive to ultraviolet (UV) light. An outer wall defines an exterior of the catheter connector. One or a plurality of UV light sources is disposed between the inner wall and the outer wall or on the outer wall positioned to emit UV light into the interior of the catheter connector. A flow sensor is provided for sensing a flow of fluid in the interior of the catheter connector, and circuitry electrically connects the UV light sources, the flow sensor and a power source, such that electrical power is supplied to the UV light sources when a fluid flows through the interior of the catheter connector.

9 Claims, 3 Drawing Sheets

(51) Int. Cl.
*A61M 16/08* (2006.01)
*A61M 25/00* (2006.01)
*A61L 2/10* (2006.01)
*A61M 39/02* (2006.01)

(52) U.S. Cl.
CPC ...... *A61L 2202/21* (2013.01); *A61M 16/0463* (2013.01); *A61M 16/0875* (2013.01); *A61M 2025/0019* (2013.01); *A61M 2039/0285* (2013.01); *A61M 2039/167* (2013.01); *A61M 2205/053* (2013.01); *A61M 2205/3334* (2013.01); *A61M 2209/10* (2013.01); *A61M 2210/1032* (2013.01); *A61M 2210/1085* (2013.01); *A61M 2210/12* (2013.01)

(56) References Cited

U.S. PATENT DOCUMENTS

| | | | | |
|---|---|---|---|---|
| 6,675,660 | B1* | 1/2004 | Mosier et al. | 73/861.07 |
| 6,877,382 | B1* | 4/2005 | Gourlay | A61B 5/087 |
| | | | | 73/514.32 |
| 7,834,328 | B2 | 11/2010 | Redmond et al. | 250/455.11 |
| 8,197,087 | B2 | 6/2012 | Sobue et al. | 362/249.02 |
| 8,381,728 | B2* | 2/2013 | Rao | A61L 2/10 |
| | | | | 128/200.26 |
| 8,585,627 | B2* | 11/2013 | Dacey, Jr. | A61L 2/0011 |
| | | | | 604/6.08 |
| 2003/0017073 | A1 | 1/2003 | Eckhardt et al. | 422/24 |
| 2005/0256447 | A1 | 11/2005 | Richardson et al. | 604/65 |
| 2007/0256226 | A1 | 11/2007 | Pinizzotto | 4/420.4 |
| 2008/0051736 | A1 | 2/2008 | Rioux et al. | 604/265 |
| 2008/0097179 | A1 | 4/2008 | Russo | 600/343 |
| 2009/0012459 | A1* | 1/2009 | Sobue | A61L 2/10 |
| | | | | 604/29 |
| 2009/0173166 | A1* | 7/2009 | Genosar | G01F 1/708 |
| | | | | 73/861.05 |
| 2010/0324505 | A1 | 12/2010 | Levenson et al. | 604/247 |
| 2012/0053512 | A1* | 3/2012 | Muse | A61M 39/16 |
| | | | | 604/21 |
| 2012/0161032 | A1 | 6/2012 | Arcand et al. | 250/454.11 |
| 2013/0281921 | A1 | 10/2013 | Sobue et al. | 604/28 |
| 2014/0264072 | A1* | 9/2014 | Abbott | A61L 9/20 |
| | | | | 250/438 |
| 2015/0037201 | A1* | 2/2015 | Armour | A61B 19/38 |
| | | | | 422/3 |

FOREIGN PATENT DOCUMENTS

| | | | |
|---|---|---|---|
| WO | WO2011107540 | 9/2011 | A61L 2/10 |
| WO | WO2013/138449 | 9/2013 | A61L 2/02 |
| WO | WO2014165854 | 10/2014 | A61L 2/10 |

OTHER PUBLICATIONS

International Preliminary Report on Patentability issued in corresponding PCT Patent Appln. PCT/US2014/070912 dated Jun. 30, 2016 (8 pgs).
Extended European Search Report issued in application No. 14871201.1, dated Sep. 12, 2017 (7 pgs).
Russian Office Action (w/machine translation) issued in application No. 2016128788/14, dated Jul. 31, 2018 (20 pgs).
Australian Office Action issued in related application No. 2014364777, dated Oct. 2, 2018 (4 pgs).
Australian Office Action issued in application No. 2014364777, dated Nov. 14, 2018 (4 pgs).
Russian Office Action issued in application No. P-1532/4RU, dated Aug. 27, 2018 (11 pgs).
Japanese Office Action (w/translation) issued in application No. 2016-560631, dated Nov. 19, 2018 (14 pgs).
Chinese Office Action (w/translation) issued in application No. 201480075554.6, dated Nov. 27, 2018 (13 pgs).

* cited by examiner

UV STERILIZING CATHETERS AND CATHETER CONNECTORS

CROSS REFERENCE TO RELATED APPLICATIONS

This Application claims priority from U.S. Provisional Application Ser. No. 61/917,818, filed Dec. 18, 2013, the contents of which are incorporated herein by reference.

FIELD

The present disclosure relates generally to catheters, and more particularly to catheters and catheter connectors including UV light for sterilization. The disclosure has particular utility in connection with sterilizing bacteria and other microbes which may be introduced to a patient through catheters and catheter connectors, as well as through a fluid flowing through catheters and/or catheter connectors, and will be described in connection with such utility, although other utilities are contemplated.

BACKGROUND

Many studies have shown that nosocomial (hospital-acquired) infections are a leading cause of death in the United States. One source of such infections involves the entry of bacteria into intraluminal access sites.

As explained in the background section of U.S. Pat. No. 7,834,328 to Redmond et al. ("Redmond"), one of the first interventions that occurs when a patient is admitted into a hospital is the placement of an intravenous access line (IV). This percutaneously-placed IV line gives the caregivers a direct path to the patient's bloodstream via a peripheral vein for rapid administration of fluids, medication or for drawing blood samples. In more serious cases, where direct access to a high blood flow supply is needed, for example, in chemotherapy delivery, temporary kidney dialysis or heart monitoring catheterization, a Central Venous Access Catheter (CVAC or Central Line) is inserted. This line is typically inserted percutaneously into a major branching vessel, frequently the subclavian vein, and then the distal segment of the catheter is directed into the superior vena cava.

Both peripheral and central catheterization procedures create an open pathway or lumen from an external access site into the bloodstream. This intraluminal access site provides an attachment point for various therapeutic or diagnostic medical devices, including, but not limited to, stopcocks, needle-less access sites, IV bags, infusion pumps, drug delivery pumps, kidney dialysis equipment, thermal dilution catheters, and the like. Unfortunately, this access site also provides an entry point for bacterial infections. Therefore, each time the access site is opened to accommodate the attachment of a medical device there is an opportunity for bacteria to enter the catheter lumen and be transferred into the bloodstream.

In addition to the contamination of the catheter lumen via the external access site, bacteria can also enter by the skin puncture and sub-cutaneous tract that is created by the catheter when the IV or CVAC is placed. Bacteria can then find their way down the outside wall of the catheter to its distal end, infecting the tract along the catheter wall as they migrate.

In an attempt to mitigate the serious problems identified in the preceding paragraphs, many prior art IV lines and CVACs use some type of molded plastic fitting at their proximal end terminated with a female Luer-lock or Luer-slip connector. These connectors must be closed by a Luer cap when not in use to prevent access site contamination. Each time the line is to be accessed, the Luer cap must be removed and discarded as it must be assumed that the outside of the Luer cap is contaminated and that once removed it is nearly impossible to prevent the male Luer configuration from touching a contaminated surface. Therefore, standard prior art infection control practice is to always replace the Luer cap whenever the line is accessed. This procedure is not only costly, but the removal and replacement process provides additional chances for bacteria to enter the lumen of the connector.

Redmond, as well as other prior techniques, is thus primarily concerned with bacterial infections that are caused by bacteria introduced into, and residing within, a Luer cap or other closure cap. To this end, Redmond discloses a substantially UV-C transparent closure cap for closing the access site, and an irradiating apparatus which fits over the transparent closure cap for irradiating the closure cap with UV-C radiation, thereby sterilizing the closure cap.

However, a drawback of the Redmond apparatus is that it requires the line to be capped, and thus cannot be sterilized while carrying a fluid to or from a patient. Further, some bacterial infections may be caused by bacteria that are not introduced via the closure cap, but rather from some point upstream of the access site. Moreover, bacteria may be introduced into a patient's body (whether into the blood stream, lungs, bladder or the like) through the fluid passing through the interior of a catheter.

See also U.S. Pat. No. 8,197,087, PCT Application Serial No. PCT/US2014/033207, and US Published Application US 2012/0053512.

Thus, a heretofore unaddressed need exists in the industry to address the aforementioned deficiencies and inadequacies.

SUMMARY

Accordingly, a primary object of this disclosure is to provide catheters and catheter connectors that may be utilized to provide UV sterilization of a fluid as it flows through the catheter and/or catheter connector. The present disclosure provides catheters and catheter connectors which not only sterilize bacteria and other microbes which may have been introduced through contamination of the connectors (e.g., as catheters are connected/disconnected), but also sterilize the fluid flowing within. Further, sterilization may be performed while the fluid flow, thus eliminating the need to cap a catheter line in order to provide sterilization.

In one aspect, the present disclosure provides a catheter connector that includes an inner wall and an outer wall. The inner wall defines an interior of the catheter connector and is transmissive to ultraviolet (UV) light. The outer wall defines an exterior of the catheter connector. The catheter connector further includes one or a plurality of UV light sources such as UV light-emitting diodes (LEDs) disposed between the inner wall and the outer wall and positioned to emit UV light into the interior of the catheter connector. Alternatively, one or a plurality of UV light-emitting diodes may be dispersed on the outer wall and positioned to emit UV light into the interior of the catheter connector. There may also be a reflective lining inserted between the inner and the outer wall to intensify the UV light beam. A flow sensor senses a flow of fluid in the interior of the catheter connector, and circuitry electrically connects the plurality of UV light sources, the flow sensor and a power source, such that electrical power is supplied to the UV light sources when a fluid flows through the interior of the catheter connector. In another aspect, the light may be turned on without requiring a sensor, e.g., by manual operation.

In another aspect, the present disclosure provides a catheter having a UV light sterilization portion. The UV light sterilization portion includes an inner wall that defines an interior of the catheter and is transmissive to ultraviolet (UV) light. An outer wall defines an exterior of the catheter. One or a plurality of UV light sources such as UV light-emitting diodes (LEDs) is disposed between the inner wall and the outer wall and is positioned to emit UV light into the interior of the catheter. Alternatively, one or a plurality of UV light sources such as UV light-emitting diodes may be disposed on the outer wall and positioned to emit UV light into the interior of the catheter. A flow sensor is provided for sensing a flow of fluid in the interior of the catheter, and circuitry electrically connects the plurality of UV light sources, the flow sensor and a power source, such that electrical power is supplied to the UV light sources when a fluid flows through the interior of the catheter.

In yet another aspect, the present disclosure provides a catheter connector that includes an inner wall defining an interior of the catheter connector and is transmissive to ultraviolet (UV) light. An outer wall defines an exterior of the catheter connector. A flow sensor senses a flow of fluid in the interior of the catheter connector. One or more optical fibers are included for transmitting UV light from a UV light source into the interior of the catheter connector. And, circuitry electrically connects the UV light source, the flow sensor and a power source, such that electrical power is supplied to the UV light source when a fluid flows through the interior of the catheter connector.

The features, functions, and advantages that have been discussed can be achieved independently in various embodiments of the present disclosure or may be combined in yet other embodiments further details of which can be seen with reference to the following description and drawings.

Other features, functions and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DESCRIPTION

Figure 1A:
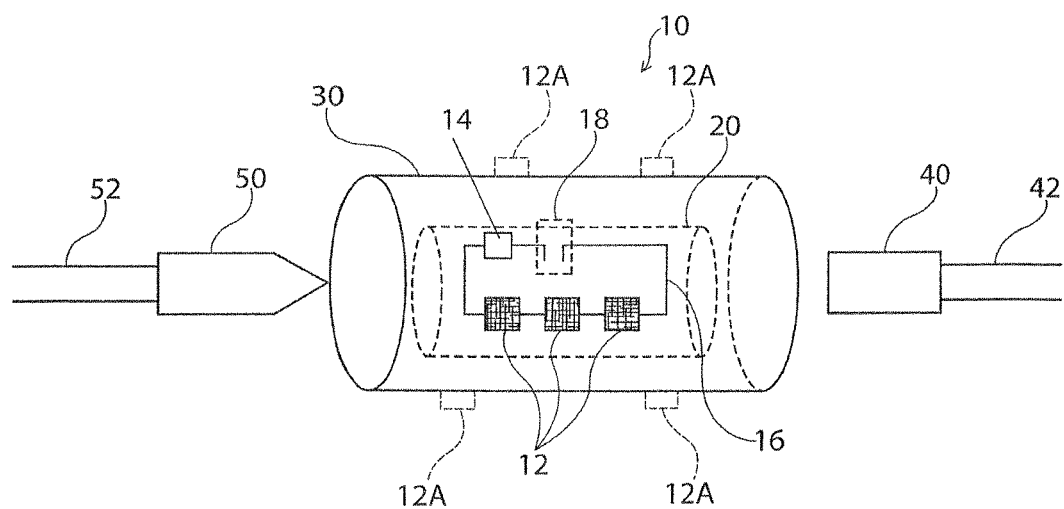
FIG. 1A is side elevation view, and FIG. 1B a cross sectional view of a catheter connector, in accordance with a first exemplary embodiment of the disclosure.
Figure 1B:
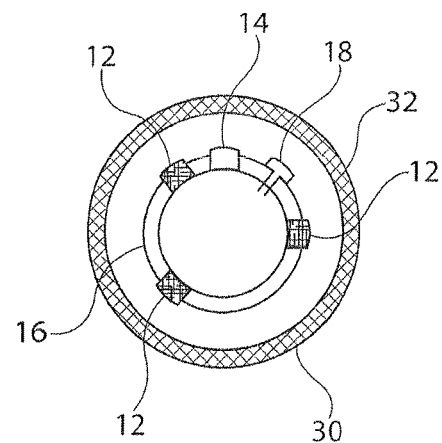

FIG. 1A and FIG. 1B are illustrations of a catheter connector 10 (hereinafter may be referred to as "connector 10"), in accordance with a first exemplary embodiment of the disclosure. The connector 10 connects a patient side of a catheter to a supply line. As used herein, "catheter" is intended to mean a medical device having a tube which may be inserted into a body cavity, duct or vessel, such as IV catheters, bladder catheters, and endotracheal tubes, and so on.

As shown in the example of FIGS. 1A and 1B, the connector 10 connects a supply port 40 of an intravenous line to a patient connector 50 of an intravenous catheter. The supply port 40 is connected to a supply line 42, which may carry a fluid to be delivered intravenously, or may receive a fluid from the patient. The patient connector 50 is connected to an intravenous catheter 52. The supply port 40 (which may be a female-type connector, as shown) and the patient connector 50 (which may be a male-type connector, as shown) may be releasably connected with one another within the connector 10. The supply port 40 and the patient connector 50 are at least partially transmissive of UV light.

The catheter connector 10 includes an inner wall 20, which defines an interior (or a lumen) of the catheter connector 10, and an outer wall 30 defining an exterior of the catheter connector 10. The inner wall 20 is at least partially transmissive of UV light. The walls 20, 30 can be formed of a plastic or any other suitable medical grade material. One or a plurality of ultraviolet (UV) light sources such as UV light-emitting diodes (LEDs) 12 are disposed in an area between the inner wall 20 and the outer wall 30, and are positioned to direct UV light inwardly, through the inner wall 20 and into the interior of the catheter connector 10. Alternatively, one or a plurality of ultraviolet (UV) light sources such as UV light-emitting diodes (LEDS) shown in phantom at 12A, may be dispersed on the outer surface of wall 30. Wall 30 should be at least partially transmissive of UV light in the area where the UV light sources are located. The UV light thus may be directed through the UV transmissive patient connector 50 and supply port 40, thereby sterilizing the inner surfaces of the inner wall 20, the patient connector 50 and the supply port 40. Further, UV light may be directed through a fluid passing through the connector 10.

Circuitry 16 electrically connects the plurality of UV light sources 12 (or 12A) to a flow sensor 18 and to a power source 14. The flow sensor 18 may be any type of sensor for sensing the presence fluid flow(liquid or gas) within a volume, in this case the interior of the catheter connector 10. For example, the flow sensor 18 may be or include a pressure sensor which may be actuated upon sensing the presence of a fluid flow, or upon sensing a flow rate of the fluid that is greater than a predetermined threshold flow rate.

In one embodiment (as shown in FIGS. 1A and 1B), the flow sensor 18 includes two electrodes which extend through the inner wall 20 and into the interior of the catheter connector 10. The electrodes, when electrically connected, complete a circuit, thereby providing power from the power source 14 to the plurality of UV light sources 12. However, the electrodes are spatially separated by a gap distance sufficient to prevent electrical current flow in certain conditions, as desired. For example, the electrodes may be separated by a distance such that current will not flow between the electrodes in a first state (i.e., in a state without a flow of a fluid of interest) and thus the circuit is "open" in such a case. However, the electrodes may be positioned close enough to one another such that current will flow between them, closing the circuit and providing power to illuminate the UV light sources, in the presence of a particular fluid having a sufficiently high electrical conductivity, e.g., blood having at least certain level of electrolyte concentration, saline solution, and so on. The distance between electrodes can be adjusted as desired to power the UV light sources in the presence of different fluid flows.

When flow of fluid is sensed by the flow sensor 18, the UV light sources are turned on, providing sterilizing UV light through the fluid flowing within the interior of the connector 10. As shown in FIG. 1a, a UV light reflector 32 may be disposed between the outer wall 30 and inner wall 20 (e.g., on an interior surface of the outer wall, between the exterior of the connector 10 and the UV light sources 12), or on the outer wall, such that UV light contacting the reflector 32 (e.g., light that passes through the fluid within the interior of the connector 10 and then through a portion of the light-transmissive inner wall 20) is reflected into the interior of the catheter connector 10. The UV light reflector may be made of any reflective material, such as etched aluminum coating, which maximizes the exposure of UV light into the interior of the connector 10 and/or a fluid flowing within.

The power source 14 may be, for example, a battery. The power source 14 may be included within the connector 10, e.g., positioned between the inner wall 20 and the outer wall 30 or on the outer wall 30, or may be located in a position physically remote from, but in electrical contact with, the connector 10.

While FIGS. 1A and 1B depict a catheter connector 10, the present disclosure is not so limited. For example, the inner wall 20, outer wall 30, plurality of UV light sources 12, 12a, circuitry 16, flow sensor 18, power source 14 and UV light reflector 32 may be incorporated within or on a patient connector 50, supply port 40 and/or the catheter line itself. Further, where these components are included within or on a catheter line, the plurality of UV light sources may be disposed within a certain segment of catheter line, or may be disposed through essentially an entire length of the catheter, thereby providing maximum UV sterilization to any fluid flowing therein.

Figure 2:
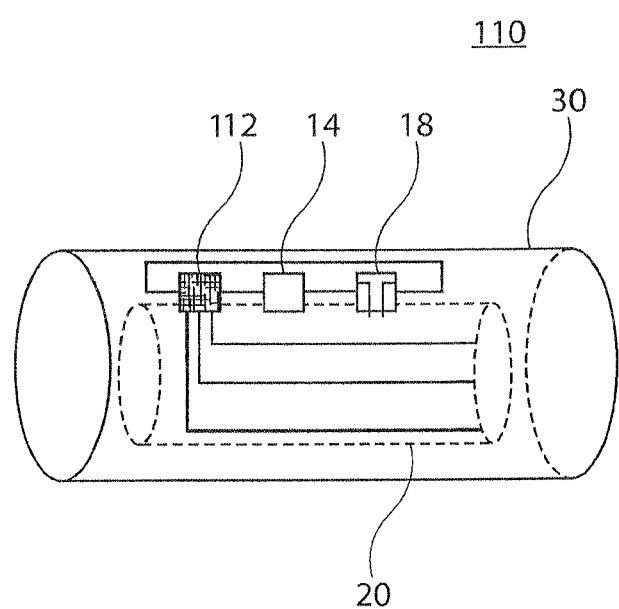
FIG. 2 is an illustration of a catheter connector, in accordance with a second exemplary embodiment of the disclosure.

FIG. 2 illustrates a catheter connector 110 (hereinafter may be referred to as "connector 110"), in accordance with a second exemplary embodiment of the disclosure. The connector 110 is substantially similar to the connector 10 of FIGS. 1A and 1B. However, the connector 110 includes optical fiber for directing the UV light to specific areas within the interior of the connector 110. The connector 110 may include one or more UV light sources 112, a power source 14 and a flow sensor 18, all electrically connected by circuitry 16, which may be electrical wiring or tracing. Further, and as in the exemplary embodiment shown in FIGS. 1A and 1B, these components may be disposed between an inner wall 20 and an outer wall 30 of the connector 110. A UV light reflector 32 may further be included in the connector 110.

The UV light source 112 provides UV light which is carried by the optical fibers 150 to desired locations within the connector 110 and/or within the interior of the connector 110. The UV light source 112 may be located within the connector 110 (for example, between inner and outer walls, as in FIG. 1), or may be located externally.

Figure 3:
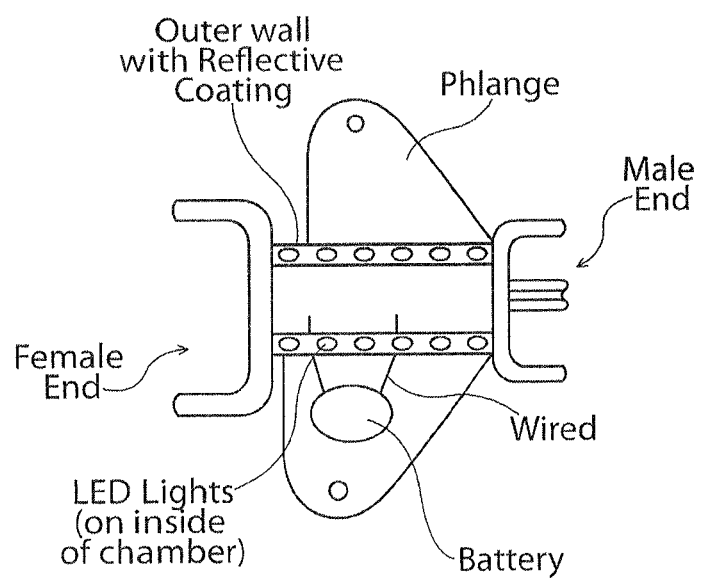
FIG. 3 is an illustration of a catheter connector, in accordance with another exemplary embodiment of the disclosure.

FIG. 3 illustrates a catheter connector, in accordance with another embodiment of the disclosure. The catheter connector shown in FIG. 3 is similar to those depicted in FIGS. 1A, 1B and 2, and includes an outer wall with an interior reflective coating, phlanges, a battery and wires, female and male ends, and LED lights disposed within an area between the outer wall and an inner wall or on the outer wall.

The present disclosure is directed to catheters and catheter connections. As used herein, "catheter" is intended to mean any medical device having a tube which may be inserted into a body cavity, duct or vessel. As such, "catheter" as used herein, is intended to include IV catheters, bladder catheters, endotracheal tubes, peritoneal dialysis catheters, and so on. Further, a "catheter connector," as used herein, is intended to include any medical connection, e.g., between a catheter and a supplying or receiving line or apparatus. For example, a catheter connector as provided herein may include a connector between a ventilator and an endotracheal tube to sterilize the air that passes into the lungs of a critically ill patient (thus reducing hospital acquired pneumonias). Further, a catheter connector may include a connector to be used between a bladder catheter and a drainage bag (thus reducing bladder infections).

It should be emphasized that the above-described embodiments of the present disclosure, particularly, any "preferred" embodiments, are merely possible examples of implementations, merely set forth for a clear understanding of the principles of the disclosure. Many other variations and modifications may be made to the above-described embodiments of the disclosure without departing substantially from the spirit and principles of the disclosure. All such modifications and variations are intended to be included herein within the scope of the present disclosure and protected by the following claims.

What is claimed is:

1. A catheter connector system releasably connecting a supply port of an intravenous line to a patient connector of an catheter, comprising:
   a connector body having:
      (a) an inner wall defining an interior of the connector body, said inner wall being transmissive to ultraviolet (UV) light; and
      (b) an outer wall defining an exterior of the connector body;
   one or a plurality of UV light sources disposed between the inner wall and the outer wall or on the outer wall and positioned to emit UV light into the interior of the connector body;
   a flow sensor for sensing a flow of fluid in the interior of the catheter;
   circuitry for electrically connecting the UV light sources, the flow sensor and a power source, such that electrical power is supplied to the UV light sources when fluid flow is sensed through the interior of the catheter;
   wherein the supply port and the inner wall of the connector body are both at least partially transmissive to UV light;
   wherein the flow sensor comprises electrodes which extend into the interior of the connector body, wherein electrical power is supplied to the UV light sources when the fluid in the interior of the connector body has a conductivity sufficient to conduct electricity between said electrodes; and
   a UV light reflector disposed between the outer wall and inner wall of the connector body or on the outer wall of the connector body and positioned to reflect UV light into the interior of the connector body and said connected supply port.

2. The catheter connector system of claim 1, wherein the UV light reflector comprises an aluminum coating.

3. The catheter connector system of claim 1, wherein the connector body is configured for use with an intravenous catheter or a bladder catheter.

4. The catheter connector system of claim 1, wherein the power source is disposed between the inner wall and the outer wall.

5. The catheter connector system of claim 1, wherein the UV light source comprises one or more UV light-emitting diodes (LEDs).

6. A catheter connector for releasably connecting a supply port of a catheter, comprising:
   a connector body having:
      (a) an inner wall defining an interior of the connector body, said inner wall and said supply port being transmissive to ultraviolet (UV) light; and
      (b) an outer wall defining an exterior of the connector body;
   one or a plurality of UV light sources disposed between the inner wall and the outer wall of the connector body or on the outer wall of the connector body and positioned to emit UV light into the interior of the catheter and the connector body;
   a flow sensor comprising a pair of spaced electrodes adapted to sense a flow of fluid in the interior of the catheter by measuring electrical conductivity of the fluid between the spaced electrodes;
   circuitry for electrically connecting the UV light sources, the flow sensor and a power source, such that electrical power is supplied to the UV light sources when fluid flow is sensed through the interior of the catheter; and
   a UV light reflector disposed between the outer wall and inner wall or on the outer wall and positioned to reflect UV light into the interior of the connector body and said connected supply port;
   wherein the catheter comprises at least one of: an IV catheter and a bladder catheter.

7. The catheter connector of claim 6, wherein the UV light source comprises one or more UV light-emitting diodes (LEDs).

8. A catheter connector system releasably connecting a supply port of an intravenous line to a patient connector of an intravenous catheter, comprising:
   a connector body having:
      (a) an inner wall defining an interior of the connector body, said inner wall being transmissive to ultraviolet (UV) light; and
      (b) an outer wall defining an exterior of the connector body;
   a flow sensor for sensing a flow of fluid in the interior of the connector body;
   one or more optical fibers for transmitting UV light from a UV light source into the interior of the connector body;
   a UV light reflector disposed between the outer wall and inner wall or on the outer wall and positioned to reflect UV light into the interior of the connector body and said connected supply port; and
   circuitry for electrically connecting the UV light source, the flow sensor and a power source, such that electrical power is supplied to the UV light source when fluid flow is sensed through the interior of the connector body;
   wherein the supply port and the inner wall of the patient connector body are both at least partially transmissive to UV light;
   wherein the flow sensor comprises electrodes which extend into the interior of the connector body, wherein electrical power is supplied to the UV light sources when the fluid in the interior of the connector body has a conductivity sufficient to conduct electricity between said electrodes.

9. The catheter connector system of claim 8, wherein the UV light source comprises one or more UV light-emitting diodes (LEDs).

* * * * *